United States Patent [19]
Haas et al.

[11] Patent Number: 5,777,003
[45] Date of Patent: Jul. 7, 1998

[54] REDISPERSIBLE POLYMER POWDER COMPOSITION COMPRISING CYCLODEXTRINS OR CYCLODEXTRIN DERIVITAVES

[75] Inventors: Wolfgang Haas, Altotting; Reiner Figge, Ampfing, both of Germany

[73] Assignee: Wacker-Chemie GmbH, Munich, Germany

[21] Appl. No.: 809,386

[22] PCT Filed: Nov. 9, 1995

[86] PCT No.: PCT/EP95/04412

§ 371 Date: Mar. 19, 1997

§ 102(e) Date: Mar. 19, 1997

[87] PCT Pub. No.: WO96/15187

PCT Pub. Date: May 23, 1996

[30] Foreign Application Priority Data

Nov. 10, 1994 [DE] Germany ............ 44 40 236.8

[51] Int. Cl.$^6$ ............ C08K 7/16; C08L 3/02
[52] U.S. Cl. ............ 523/223; 524/48
[58] Field of Search ............ 524/48; 523/223

[56] References Cited

U.S. PATENT DOCUMENTS

| | | | |
|---|---|---|---|
| 3,565,887 | 2/1971 | Parmerter et al. | 536/103 |
| 4,582,900 | 4/1986 | Braudt et al. | 536/103 |
| 5,004,767 | 4/1991 | Krause et al. | 524/48 |
| 5,055,504 | 10/1991 | Mahil et al. | 524/48 |
| 5,147,907 | 9/1992 | Rinck et al. | 524/48 |
| 5,274,016 | 12/1993 | Berner et al. | 524/109 |
| 5,480,924 | 1/1996 | Vieil et al. | 524/48 |
| 5,492,947 | 2/1996 | Wood et al. | 524/48 |

FOREIGN PATENT DOCUMENTS

| | | |
|---|---|---|
| 2079726 | 8/1993 | Canada . |
| 0134451 | 3/1985 | European Pat. Off. . |
| 0146841 | 7/1985 | European Pat. Off. . |
| 0355685 | 2/1990 | European Pat. Off. . |
| 0408099 | 1/1991 | European Pat. Off. . |
| 0536597 | 4/1993 | European Pat. Off. . |

OTHER PUBLICATIONS

Translation to 0134451 by Janet Thompson C10 Europe House.

Derwent Abstract (AN 83-816629) corresponds to JP-A 58168603.

Derwent Abstract (AN 30-059839) corresponds to EP -A 355685.

*Primary Examiner*—Kriellions S. Morgan
*Attorney, Agent, or Firm*—Burgess, Ryan & Wayne

[57] ABSTRACT

Redispersable polymer powder compositions are provided which contain homopolymers or copolymers of ethylenically unsaturated monomers and cyclodextrins or cyclodextrin derivatives having the general formula (I).

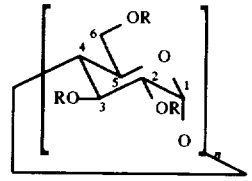

in which n=6, 7 or 8, the substituents R are identical or different and cover H or $R^1$, the substituents $R^1$ are identical or different and cover for optionally substituted $C_1$-$C_4$-alkyl, carboxy-$C_1$-$C_4$-alkyl, $C_2$-$C_4$-carboxyly residues. Also disclosed are a process for preparing these compositions and their use, as well as polymer dispersions stabilised with cyclodextrins or cyclodextrin derivatives obtained as intermediate products.

13 Claims, No Drawings

REDISPERSIBLE POLYMER POWDER COMPOSITION COMPRISING CYCLODEXTRINS OR CYCLODEXTRIN DERIVITAVES

BACKGROUND OF THE INVENTION

1) Field of the Invention

The invention relates to redispersible polymer powder compositions which comprise homo- or copolymers of ethylenically unsaturated monomers and cyclodextrins or cyclodextrin derivatives; processes for their preparation and their use. The invention furthermore relates to the polymer dispersions which are obtainable as intermediate products and are stabilized with cyclodextrins or cyclodextrin derivatives.

2) Background Art

Redispersible powders which can be prepared from dispersions of the most diverse polymers are gaining ever increasing importance for the most diverse uses. In general, dispersions stabilized with a protective colloid and/or emulsifier are used as the starting substances for the preparation of these powders. These dispersions are dried in a known manner and at the same time or subsequently are protected against blocking during storage by means of additives. The protective colloids used are, for example, synthetically prepared water-soluble homo- and copolymers or natural products, such as cellulose derivatives and starch derivatives. However, in spite of the addition of protective colloids, many known dispersions cannot be dried to give redispersible powders.

The preparation of redispersible polymer powders which are obtainable by drying polymer dispersions prepared by polymerization in the presence of starch and/or starch derivatives is known from EP-A 134451. Dextrins accessible by hydrolysis of starch are described as starch derivatives.

EP-A 536597 (CA-A 2079726) discusses the preparation of aqueous polymer dispersions in the presence of roasted dextrins accessible by the action of heat on starch. The Application furthermore relates to the preparation of aqueous polymer dispersions in the presence of starch degradation products of bimodal molecular weight distribution accessible by hydrolysis in an aqueous phase. It furthermore relates to the preparation of polymer powders by drying the aqueous polymer dispersions mentioned.

EP-A 408099 (U.S. Pat. No. 5147907) relates to the preparation of aqueous polymer dispersions in which the polymerization is carried out in the presence of roasted dextrins having a molecular weight of >5000. The use of low molecular weight starch degradation products is advised against.

A disadvantage of all the procedures mentioned is that if starch degradation products such as dextrins, which are obtainable by acid hydrolysis (acid dextrins) or by heat treatment (roasted dextrins), are used, a mixture of longer or shorter, branched or unbranched glucose chains is present rather than defined compounds. The molecular weight can vary over a relatively wide range and can be stated only in ranges. As a consequence of the variation, the polymerization result is not reliably reproducible when such mixtures are used; variations occur in respect of product quality of the polymer dispersions, which can also have an effect on the properties of redispersible polymer powders prepared therefrom. In spite of the addition of starch degradation products as a protective colloid, many dispersions cannot be dried to give redispersible powders. The powder properties and the use properties of products prepared in this way furthermore are subject to wide variations which are influenced on the one hand by the raw material basis used and on the other hand by the hydrolysis process.

SUMMARY OF THE INVENTION

There was therefore the object of providing re-dispersible polymer powders, the use properties of which can be adjusted reliably by using, as protective colloids, compounds which have the lowest possible molecular weight and the lowest possible range in variation in respect of their composition.

This object is achieved with polymer powders which comprise cyclodextrins or cyclodextrin derivatives.

It is known from EP-A 355685 to employ cyclo-dextrins as foam suppressants in polymer dispersions. JP-A 58168603 (Derwent Abstract AN 83-816629) describes the use of lipophilic cyclodextrin derivatives in the polymerization of two-phase systems of water and an organic solvent.

DESCRIPTION OF THE PREFERRED EMBODIMENTS

The invention relates to redispersible polymer powder compositions which comprise homo- or copolymers of ethylenically unsaturated monomers and cyclodextrins or cyclodextrin derivatives of the general formula

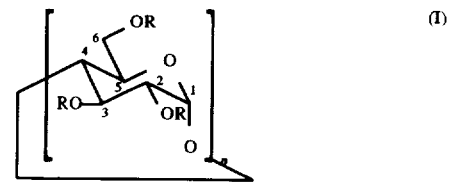

in which $n=6$, 7 or 8 and R is identical or different and has the meaning of H or $R^1$, where $R^1$ is identical or different and has the meaning of optionally substituted $C_1$–$C_4$-alkyl, hydroxy-$C_1$–$C_4$-alkyl, carboxy-$C_1$–$C_4$-alkyl or $C_2$–$C_4$-carboxyl radicals.

Suitable homo- or copolymers comprise one or more monomer units from the group consisting of vinyl esters of unbranched or branched carboxylic acids having 1 to 18 C atoms, from the group consisting of esters of acrylic acid and methacrylic acid with unbranched or branched alcohols having 1 to 18 C atoms, from the group consisting of vinylaromatics, from the group consisting of vinyl halides and from the group consisting of olefins.

Preferred vinyl esters are vinyl acetate, vinyl propionate, vinyl butyrate, vinyl 2-ethylhexanoate, vinyl laurate, 1-methylvinyl acetate, vinyl pivalate and vinyl esters of α-branched monocarboxylic acids having 5 or 9 to 10 C atoms, for example VV5®, VeoVa9® or VeoVa10® (Shell corporation's vinyl esters of versatic acids). Vinyl acetate is particularly preferred.

Preferred methacrylic acid esters or acrylic acid esters are methyl acrylate, methyl methacrylate, ethyl acrylate, ethyl methacrylate, propyl acrylate, propyl methacrylate, n-butyl acrylate, n-butyl methacrylate, iso-butyl acrylate, iso-butyl methacrylate, t-butyl acrylate, t-butyl methacrylate, 2-ethylhexyl acrylate and 2-ethylhexyl methacrylate. Methyl acrylate, methyl methacrylate, n-butyl acrylate and 2-ethylhexyl acrylate are particularly preferred. Preferred vinylaromatics are styrene, α-methyl-styrene, o-chlorostyrene or vinyltoluenes.

Preferred vinyl halides are vinyl chloride and vinylidene chloride.

Preferred olefins are ethylene, propylene, 1,3-butadiene and isoprene.

If appropriate, the vinyl ester copolymers can comprise 1.0 to 50% by weight, based on the total weight of the copolymer, of α-olefins, such as ethylene or propylene, and/or vinylaromatics, such as styrene, and/or vinyl halides, such as vinyl chloride, and/or acrylic acid esters or methacrylic acid esters of alcohols having 1 to 12 C atoms, such as methyl acrylate, methyl methacrylate, ethyl acrylate, ethyl methacrylate, propyl acrylate, propyl methacrylate, n-butyl acrylate, n-butyl methacrylate or 2-ethylhexyl acrylate, and/or ethylenically unsaturated dicarboxylic acid esters or derivatives thereof, such as diisopropyl fumarate, di-t-butyl fumarate, the dimethyl, dibutyl and diethyl esters of maleic acid or fumaric acid, maleic anhydride or acrylonitrile. The choice of the monomers mentioned is preferably here such that copolymers having a glass transition temperature $T_g$ of −30° C. to +40° C. are obtained.

If appropriate, the (meth)acrylic acid ester copolymers can comprise 1.0 to 50% by weight, based on the total weight of the copolymer, of a-olefins, such as ethylene or propylene, and/or vinylaromatics, such as styrene, and/or vinyl halides, such as vinyl chloride, and/or ethylenically unsaturated dicarboxylic acid esters or derivatives thereof, such as diisopropyl fumarate, di-t-butyl fumarate, the dimethyl, dibutyl and diethyl esters of maleic acid or fumaric acid, maleic anhydride or acrylonitrile. The choice of the monomers mentioned is preferably taken here such that copolymers having a glass transition temperature $T_g$ of −30° C. to +40° C. are obtained.

If appropriate, the polymers mentioned also comprise 0.05 to 30.0% by weight, preferably 0.5 to 15% by weight, in each case based on the total weight of the polymer, of one or more auxiliary monomer units to improve water-solubility, for crosslinking or for modification of the adhesion properties.

Suitable auxiliary monomers for improving the water-solubility are, for example, α,β-monoethylenically unsaturated mono- and dicarboxylic acids and amides thereof, such as acrylic acid, methacrylic acid, maleic acid, fumaric acid, itaconic acid, acrylamide and methacrylamide; and ethylenically unsaturated sulfonic acids and salts thereof, preferably vinylsulfonic acid, 2-acrylamido-propanesulfonate and/or N-vinylpyrrolidone.

The polymer preferably comprises monomer units having a crosslinking action to the extent of 0.5 to 5.0% by weight, based on the total weight of the polymer. Examples of these are N-methylolacrylamide and N-methyl-olmethacrylamide; N-(alkoxymethyl)acrylamides or N-(alkoxymethyl) methacrylamides with a $C_1$- to $C_6$-alkyl radical, such as N-(isobutoxymethyl)-acrylamide (IBMA), N-(isobutoxymethyl)-methacrylamide (IBMMA), N-(n-butoxy-methyl) -acrylamide (NBMA) and N-(n-butoxymethyl) -meth-acrylamide (NBMMA); and poly-ethylenically unsaturated comonomers, such as ethylene glycol diacrylate, 1,3-butylene glycol diacrylate, 1,4-butylene glycol diacrylate, propylene glycol diacrylate, divinyl adipate, divinyl-benzene, vinyl methacrylate, vinyl acrylate, allyl methacrylate, allyl acrylate, diallyl maleate, diallyl phthalate, diallyl fumarate, methylenebisacrylamide, cyclopentadienyl acrylate or triallyl cyanurate.

Comonomer units which are suitable for modification of the adhesion properties are, for example, hydroxyalkyl esters of methacrylic acid and acrylic acid, such as hydroxyethyl, hydroxypropyl or hydroxybutyl acrylate or methacrylate, and compounds such as di-ace-toneacrylamide and acetylacetoxyethyl acrylate or methacrylate.

Preferred vinyl ester polymers comprise as monomer units, in each case based on the total weight of the polymer:

50 to 100% by weight of vinyl ester, in particular vinyl acetate;

50 to 95% by weight of vinyl ester, in particular vinyl acetate, and 5 to 50% by weight of α-olefin, in particular ethylene;

50 to 75% by weight of vinyl acetate, 1 to 30% by weight of vinyl laurate or vinyl ester of an α-branched carboxylic acid in particular versatic acid vinyl ester, and 5 to 40% by weight of ethylene;

70 to 99% by weight of vinyl acetate and 1 to 30% by weight of vinyl laurate or vinyl ester of an α-branched carboxylic acid, in particular versatic acid vinyl ester;

70 to 99% by weight of vinyl ester, in particular vinyl acetate, and 1 to 30% by weight of acrylic acid ester, in particular n-butyl acrylate or 2-ethylhexyl acrylate;

50 to 75% by weight of vinyl acetate, 1 to 30% by weight of acrylic acid ester, in particular n-butyl acrylate or 2-ethylhexyl acrylate, and 5 to 40% by weight of ethylene; or 30 to 75% by weight of vinyl acetate, 1 to 30% by weight of vinyl laurate or vinyl ester of an α-branched carboxylic acid, in particular versatic acid vinyl ester, 1 to 30% by weight of acrylic acid ester, in particular n-butyl acrylate or 2-ethylhexyl acrylate, and 5 to 40% by weight of ethylene.

Preferred (meth)acrylic acid ester polymers comprise as monomer units, in each case based on the total weight of the polymer: 35 to 65% by weight of methyl methacrylate and 65 to 35% by weight of n-butyl acrylate and/or 2-ethylhexyl acrylate; or 35 to 65% by weight of styrene and 65 to 35% by weight of n-butyl acrylate and/or 2-ethylhexyl acrylate.

The vinyl ester polymers and (meth)acrylic acid ester polymers mentioned as preferred can furthermore also comprise the abovementioned auxiliary monomers in the amounts mentioned. The data in % by weight for the monomer contents in the preferred vinyl ester and (meth)acrylic acid ester polymers mentioned in each case add up to 100% by weight.

Suitable cyclodextrins are α-cyclodextrin (cyclohexaamylose, formula I: n=6, R=H), β-cyclodextrin (cycloheptaamylose, formula I: n=7, R=H) γ-cyclodextrin (cyclooctaamylose, formula I: n=8, R=H) or mixtures of the cyclodextrins mentioned.

The cyclodextrins are accessible in a pure form by enzymatic cleavage of starch with cyclodextrin glycosyl transferases (CGTases) and subsequent working up of the cyclodextrin mixtures obtained by this cleavage by means of chromatographic separation or separation by means of complexing agents. Such processes are described, for example in DE-A 4324650. α-, β- and γ-cyclodextrin are moreover commercially obtainable.

Examples of cyclodextrin derivatives are, from the group consisting of cyclodextrin alkyl ethers, the methyl ether ethyl ethers or propyl ethers of α-, β- and γ-cyclodextrin Examples from the group consisting of the hydroxyalkyl ethers are hydroxyethyl, hydroxypropyl and dihydroxypropyl ethers of α-, β- and γ-cyclodextrin. Examples from the group consisting of the carboxyalkyl ethers are carboxymethyl and carboxypropyl ethers of α-, β- and γ-cyclodextrin and alkali metal salts thereof, such as the sodium carboxymethyl ether. Suitable cyclodextrin ethers are also mixed ethers of α-, β- and γ-cyclodextrin which contain at least two different groups of the alkyl ether, hydroxyalkyl ether carboxy-alkyl ether groups mentioned. Examples of cycl dextrin esters are the acetic acid esters (acetyl-cyclodextrins) and propionic acid esters (propionyl-cyclodextrins) of α-, β- and γ-cyclodextrin. Examples of substituted cyclodextrin ethers or cyclodextrin esters are 2-amino-ethyl- or 2-chloroacetyl-cyclodextrins.

Preferred cyclodextrin derivatives are the methyl ethers, hydroxypropyl ethers, carboxymethyl ethers and the acetic acid esters of α-, β- and γ-cyclodextrin.

Substituted cyclodextrins are also characterized by their average degree of substitution (DS value). The DS value indicates how many substituents on average are bonded to the O2, O3 and/or O6 position per anhydroglucose unit. The DS value can be determined, for example, via $^1$H-NMR spectroscopy. The degree of substitution of the cyclodextrin derivatives is preferably 0.5 to 2.5.

Processes for the preparation of the cyclodextrin derivatives mentioned are known to the expert and are described, for example, in EP-A 146841 (U.S. Pat. No. 4582900) and U.S. Pat. No. 3565887.

The polymer powder compositions preferably comprise 0.3 to 20% by weight of cyclodextrin or cyclodextrin derivatives, based on the polymer content. If appropriate, the polymer powder compositions also comprise other additives, such as spraying aids, anti-foams and/or anti-blocking agents.

The invention furthermore relates to a process for the preparation of the redispersible polymer powder compositions which comprise homo- or copolymers of ethylenically unsaturated monomers and cyclodextrin or cyclodextrin derivatives of the general formula (I) by a) emulsion polymerization of one or more ethylenically unsaturated monomers by means of free radical initiators in an aqueous medium in the presence of cyclodextrin or cyclodextrin derivatives of the general formula (I) and if appropriate emulsifiers and in the absence of protective colloids and b) drying of the aqueous polymer dispersion obtained by this procedure, if appropriate with the addition of antiblocking agents and/or further additives.

The aqueous polymer dispersions are prepared by the process of aqueous emulsion polymerization in the presence of 0.3 to 10.0% by weight, based on the total weight of the monomers, of cyclodextrin or cyclodextrin derivatives of the formula (I). The polymerization temperature is as a rule 35°–95° C., preferably 40°–80° C. The polymerization medium employed is water, or if appropriate a mixture of water and solvents which are readily miscible with water, such as acetone or ethanol. The polymerization is preferably carried out in water. The polymerization can be carried out by the batch process, in which all the components are initially introduced into the reactor, and by the metering process, in which individual or several components are fed in during the polymerization. Mixed types with an initial mixture and metering are preferred. The meterings can be carried out separately (with respect to space and time), or the components to be metered can be metered entirely or in part in pre-emulsified form. The cyclodextrins or cyclodextrin derivatives can be initially introduced into the reactor or metered in, or distributed between the initial mixture and metering. Preferably, the cyclodextrins or cyclodextrin derivatives are initially introduced into the reactor. The meterings can be carried out at a constant rate and at varying rates. The same provisos as for the use of the other reaction components apply to the use of the initiator system.

If, for example, gaseous reaction components are to be employed, the emulsion polymerization can also be carried out under increased pressure. If the polymerization is carried out under pressure, for example if the monomers vinyl chloride or ethylene are employed, pressures of 5 bar to 80 bar are preferred. The target amount of ethylene which is to be copolymerized, for example, is decisive.

The cyclodextrins and derivatives of the formula (I) to be used according to the invention can be employed both by themselves and in combination with emulsifiers. Possible concomitant emulsifiers are anionic, cationic and also nonionic emulsifiers. If the polymerization is carried out in the presence of emulsifiers, the amount thereof is preferably up to 4% by weight, based on the total weight of the monomer phase. Anionic and nonionic emulsifiers are preferably employed. Customary emulsifiers are, for example, ethoxylated fatty alcohols with a $C_8$–$C_{36}$-alkyl radical and a degree of ethoxylation (degree of EO) of 3 to 50; ethoxylated mono-, di- and trialkylphenols with a $C_4$–$C_{10}$-alkyl radical and a degree of EO of 3 to 50; and alkali metal salts of di-$C_4$–$C_{12}$-alkyl esters of sulfosuccinic acid. Alkali metal and ammonium salts of $C_8$–$C_{12}$-alkyl sulfates, of ethoxylated alkanols with a $C_{12}$–$C_{18}$-alkyl radical and a degree of EO of 3 to 30, of ethoxylated $C_4$–$C_{10}$-alkylphenols having a degree of EO of 3 to 50, of $C_{12}$–$C_{18}$-alkylsulfonic acids, of $C_9$–$C_{18}$-alkylarylsulfonic acids and of sulfonates of ethoxylated, linear and branched $C_8$–$C_{36}$-alkyl alcohols having a degree of EO of 3 to 50 are also suitable.

The initiation of the polymerization is carried out with the water-soluble thermal initiators or redoxinitiator combinations customary for emulsion polymerization. Examples of thermal initiators are organic peroxides, such as tert-butyl hydroperoxide or cumyl hydroperoxide, or peroxodisulfates, such as potassium peroxodisulfate or ammonium peroxodisulfate, or $H_2O_2$ or azo compounds, such as azodiisobutyronitrile. Redox initiators which are used are preferably hydrogen peroxide, tert-butyl hydroperoxide, potassium peroxodisulfate or ammonium peroxodisulfate in combination with hydroxymethanesulfinic acid, ascorbic acid or sodium sulfite as the reducing agent. The reactivity of the initiator system is expediently increased by addition of metal ions which can occur in several valency levels. $Fe^{2+}$ or $Ce^{2+}$ ions are preferably used. The amount of initiator is preferably 0.01 to 1.0% by weight, based on the total weight of the monomer phase.

To control the molecular weight, regulating substances can be employed during the polymerization. They are usually employed in amounts of between 0.01 and 5.0% by weight, based on the monomers to be polymerized, and are metered in separately or else as a premix with the reaction components. Examples of such substances are dodecylmercaptan, mercaptopropionic acid, methyl mercaptopropionate, isopropanol and acetaldehyde.

The aqueous dispersions obtainable by the process according to the invention have a solids content of 30 to 75% by weight, preferably 40 to 65% by weight.

The invention furthermore relates to aqueous polymer dispersions having a solids content of 30 to 75% by weight which comprise homo- or copolymers of ethylenically unsaturated monomers and cyclodextrin or cyclodextrin derivatives of the general formula (I) and are obtainable by emulsion polymerization of one or more ethylenically unsaturated monomers by means of free radical initiators in an aqueous medium in the presence of cyclodextrin or cyclodextrin derivatives of the general formula (I), and if appropriate an emulsifier, and in the absence of protective colloids.

To prepare the redispersible polymer powder compositions, the aqueous dispersions are finally dried. Suitable drying processes are, for example, spray drying, freeze drying, roller drying, belt drying or disk drying. The dispersions are preferably spray dried or freeze dried.

Spray drying of the dispersions is most preferred. The known devices, such as, for example, spraying through one-, two- or multicomponent nozzles or with a rotating disk, in a stream of dry gas, preferably air, which is heated if appropriate, can be resorted to here. In general, temperatures above 250° C. are not used as the intake temperature of the dry gas. The discharge temperatures of the dry gas are in general in the range from 45° to 100° C., preferably 55° to 90° C., depending on the unit, the polymer composition and the desired degree of drying.

For drying, the dispersions are brought to a solids content of 10 to 75% by weight, preferably 30 to 65% by weight. The solids content depends on the drying process chosen and on the nature and amount of further additives which are added during drying. For the preferred spray drying, a viscosity of the overall system of up to 1000 mPa.s has proved appropriate.

For example, spraying aids can be added to the dispersion before the drying. They are preferably added in the form of their aqueous solutions in amounts of preferably 5 to 40% by weight, in particular 5 to 20% by weight, based on the polymer. The optimum amount depends on the stabilization of the dispersion, the glass transition temperature of the polymers contained therein and the desired properties of the powder.

Suitable spraying aids are, inter alia, by themselves or in combination, cyclodextrins, cyclodextrin derivatives, degraded or modified starches, starch derivatives, cellulose derivatives and water-soluble polymers, in particular those having high glass transition temperatures of at least 50° C. Examples of such polymers, which are often commercially available, are: vinyl alcohol copolymers (polyvinyl alcohol) having a degree of hydrolysis of 85 to 94 mol% and a Höppler viscosity, determined in 4% strength solution, of 3 to 25 mPa.s; completely hydrolyzed copolymers of vinyl acetate and alkyl vinyl esters having a Höppler viscosity of 1 to 25 mPa.s; vinylpyrrolidone (co)polymers; ligninsulfonates; water-soluble sulfonate group-containing condensates of melamine and formaldehyde or naphthalene and formaldehyde; phenolsulfonic acid-formaldehyde condensates; polyacrylamides; copolymers of styrene and maleic acid and/or itaconic acid and esters thereof; water-soluble copolymers of olefinically unsaturated acids and alkenes; and water-soluble copolymers of monomers such as acrylic acid, methacrylic acid, itaconic acid, fumaric acid, methyl, ethyl and butyl (meth)acrylate, ethylhexyl acrylate, decyl acrylate and hydroxyethyl and hydroxypropyl (meth) acrylate.

A content of up to 1.5% by weight of antifoam, based on the base polymer, has often proved to be favorable during the spraying. Liquid antifoams are usually added to the dispersion before drying, while solid antifoams can be mixed into the dry dispersion powder composition.

To improve the storage stability by improving blocking stability, in particular in powders with a low glass transition temperature, an antiblocking agent (anticaking agent), preferably up to 30% by weight, based on the total weight of polymeric constituents, can be added to the resulting powder. This is preferably done while the powder is still finely divided, for example still suspended in the dry gas. In particular, the antiblocking agent is metered into the drying device separately from but at the same time as the dispersion. Examples of antiblocking agents are finely ground aluminum silicates, kieselguhr, colloidal silica gel, pyrogenic silicic acid, precipitated silicic acid, microsilica, ground gypsum, kaolin, talc, cements, diatomaceous earth, calcium carbonate or magnesium hydrosilicate.

The dispersion powders according to the invention are suitable for use in the building industry, in particular as additives to hydraulic binders, such as cement and gypsum, in particular use in concrete, building adhesives, mortars, stopping compositions and flow control compositions. The dispersion powders are furthermore suitable as binders for coating, plasters and coverings, in particular paints; as adhesives for wood, paper and textiles; as binders in papermaking; as binders for compression molding compositions and shaped articles and as binders for the production of compression-molded articles which comprise active compounds and are preferably produced by direct pressing.

The dispersion powders prepared according to the invention improve the processing properties in mortars, drastically reduce the amount of mixing water required and significantly improve the mechanical properties, such as adhesion and flexural tensile strength, of hardened mortars.

The following Examples and Comparison Examples serve to further illustrate the invention:

For comparison of the properties of dispersion powders comprising a cyclodextrin (derivative) with those powders without a cyclodextrin (derivative) content, styrene/butyl acrylate and vinyl acetate/ethylene powders were prepared as comparison powders without the addition of cyclodextrins or cyclodextrin derivatives. Preparation of the polymer dispersions:

COMPARISON EXAMPLE 1

101 kg of completely desalinated water, 3.0 kg of a 20% strength aqueous solution of the sodium salt of dihexylsulfosuccinate and 1.65 kg of 10% strength acetic acid were initially introduced into an autoclave. The pH of the initial mixture was brought to 4.0 with 10% strength sodium hydroxide solution. 22.5 kg of vinyl acetate were emulsified in, while stirring, and the mixture was heated up to 75° C. When temperature equilibrium had been reached, ethylene was forced in up to 20 bar. Metering of solutions of 630 g of potassium peroxodisulfate in 20.4 kg of water and 316 g of hydroxymethanesulfinic acid in 20.8 kg of water was then started simultaneously. After the start of the reaction, 203 kg of vinyl acetate were allowed to run in. A solution of 113 kg of water, 20 kg of 30% strength sodium lauryl polyglycol sulfate and 2.25 kg of 50% strength sodium acrylamido-2 methylpropanesulfonate was also metered in. When the monomer and emulsifier feed had ended, also no further ethylene was fed in, and the initiator system was still metered in further until the solids content of the dispersion no longer rose. The mixture was then cooled and the autoclave was let down. To bring the polymerization to completion, 1.94 kg of 10% strength aqueous tert-butyl hydroperoxide solution and 1.94 kg of 10% strength aqueous hyroxymethanesulfinic acid solution were now added.

An ethylene/vinyl acetate copolymer with an ethylene content of 15.0% by weight, a vinyl acetate content of 84.6% by weight and 0.4% by weight of AMPS resulted. The dispersion had no coarse fraction, and had a solids content of 49.8% by weight, a pH of 4.0 and an average particle size of 310 nm.

COMPARISON EXAMPLE 2

349 g of completely desalinated water, 5.12 g of a 20% strength aqueous solution of the sodium salt of dihexylsulfosuccinate and 6.00 g of 10% strength acetic acid were initially introduced into a glass reactor. The pH of the initial mixture was brought to 4.0 with 10% strength sodium hydroxide solution. 41.0 g each of styrene and butyl acrylate were emulsified in, while stirring, and the mixture was heated up to 50° C. 320 g of water, 55.6 g of 30% strength sodium lauryl polyglycol sulfate, 81.9 g of 30% strength acrylamide, 369 g of styrene and 369 g of butyl acrylate were pre-emulsified in a metering container. The pH of the pre-emulsion was brought to 4.0 with 10% strength acetic acid. Metering in of solutions of 12.9 g of 40% strength tert-butyl hydroperoxide in 159 g of water and 8.82 g of hydroxy-5 methanesulfinic acid in 163 g of water was then started simultaneously, while stirring. After the start of the reaction, the pre-emulsion was metered in uniformly. When the pre-emulsion feed had ended, the initiator system was still metered in further until the solids content of the dispersion no longer rose. The mixture was then cooled. To bring the polymerization to completion, 5.3 ml of 10% strength aqueous tert-butyl hydroperoxide solution and 4.3 ml of 10% strength aqueous hydroxymethanesulfinic acid solution were now added.

A styrene/butyl acrylate copolymer with a styrene content of 48.5% by weight, a butyl acrylate content of 48.5% by weight and 3.0% by weight of acrylamide resulted. The dispersion had no coarse fraction and had a solids content of 49.0% by weight, a pH of 3.5 and an average particle size of 210 nm.

EXAMPLE 1

17.0 kg of completely desalinated water, 923 g of a 20% strength aqueous solution of the sodium salt of dihexylsulfosuccinate, 270 g of 10% strength acetic acid and 1.85 kg of a-cyclodextrin were initially introduced into a polymerization tank. The pH of the initial mixture was brought to 4.1 with 10% strength sodium hydroxide solution. 1.85 kg each of styrene and butyl acrylate were emulsified in, while stirring, and the mixture was heated up to 50° C. 14.4 kg of water, 2.46 kg of 30% strength sodium lauryl polyglycol sulfate, 3.69 kg of 30% strength acrylamide, 16.6 kg of styrene and 16.6 kg of butyl acrylate were pre-emulsified in a metering container. The pH of the pre-emulsion was brought to 4.1 with 10% strength acetic acid. Metering of solutions of 581 g of 40% strength tert-butyl hydroperoxide in 7.17 kg of water and 399 g of hydroxymethanesulfinic acid in 7.39 kg of water was then started simultaneously, while stirring. After the start of these meterings, the pre-emulsion was metered in. When the pre-emulsion feed had ended, the initiator system was still metered in further until the solids content of the dispersion no longer rose. The mixture was then cooled. To bring the polymerization to completion, 240 ml of 10% strength aqueous tert-butyl hydroperoxide solution and 240 g of 10% strength aqueous hydroxymethanesulfinic acid solution were now added.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 44.6% by weight, a pH of 3.7 and an average particle size of 350 nm.

EXAMPLE 2

The procedure was analogous to Example 1, with the difference that 1.85 kg of β-cyclodextrin was used as the cyclodextrin.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 48.2% by weight, a pH of 4.4 and an average particle size of 300 nm.

EXAMPLE 3

The procedure was analogous to Example 1, with the difference that 1.85 kg of γ-cyclodextrin was used as the cyclodextrin.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 46.7% by weight, a pH of 3.7 and an average particle size of 260 nm.

EXAMPLE 4

The procedure was analogous to Example 1, with the difference that 1.85 kg of acetyl-β-cyclodextrin with a degree of substitution of DS=1.0 was used as the cyclodextrin.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 46.2% by weight, a pH of 3.3 and an average particle size of 290 rm.

EXAMPLE 5

The procedure was analogous to Example 1, with the difference that 1.85 kg of hydroxypropyl-β-cyclo-dextrin with a degree of substitution of DS=0.9 was used as the cyclodextrin.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 45.7% by weight, a pH of 3.4 and an average particle size of 300 mm.

EXAMPLE 6

The procedure was analogous to Example 5, with the difference that 0.75 kg of hydroxypropyl-β-cyclo-dextrin with a degree of substitution of DS=0.9 was used.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 46.9% by weight, a pH of 4.0 and an average particle size of 1700 nm.

EXAMPLE 7

The procedure was analogous to Example 1, with the difference that 1.85 kg of methyl-β-cyclodextrin with a degree of substitution of DS=0.6 was used as the cyclodextrin.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 44.8% by weight, a pH of 4.1 and an average particle size of 2000 nm.

EXAMPLE 8

The procedure was analogous to Example 1, with the difference that 1.85 kg of carboxymethyl-β-cyclo-dextrin with a degree of substitution of DS=0.3 was used as the cyclodextrin.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 43.2% by weight, a pH of 4.2 and an average particle size of 300 nm.

EXAMPLE 9

2580 g of completely desalinated water, 127 g of a 20% strength aqueous solution of the sodium salt of dihexylsulfosuccinate, 46.5 ml of 10% strength acetic acid and 317 g of acetyl-$\beta$-cyclodextrin (degree of substitution 1.0) (Ac-$\beta$-CD, DS=1.0) were initially introduced into a pressure reactor. The pH of the initial mixture was 4.0. 635 g of vinyl acetate were emulsified in, while stirring, and the mixture was heated up to 75° C. When temperature equilibrium had been reached, up to 25 bar of ethylene were forced in. Metering of solutions of 47.7 g of potassium peroxodisulfate in 1540 g of water and 23.8 g of hydroxymethanesulfinic acid in 1560 g of water were then started simultaneously. After the start of the reaction, 5710 g of vinyl acetate and a solution of 265 g of 30% strength sodium lauryl polyglycol sulfate and 79.4 g of 50% strength sodium acrylamido-2-methylpropanesulfonate in 3960 g of water were metered in. When the monomer and emulsifier feed had ended, no further ethylene was fed in and the initiator system was still metered in further until the solids content of the dispersion no longer rose. The mixture was then cooled and the autoclave was let down. To bring the polymerization to completion, 55 g of 10% strength aqueous tert-butyl hydroperoxide solution and 55 g of 10% strength aqueous hydroxymethanesulfinic acid solution were now added.

An ethylene/vinyl acetate copolymer with an ethylene content of 15% by weight, a vinyl acetate content of 84.6% by weight and 0.4% by weight of AMPS resulted. The dispersion had no coarse fraction and had a solids content of 50.5% by weight, a pH of 3.2 and an average particle size of 570 nm.

EXAMPLE 10

The procedure was analogous to Example 9, with the difference that 131 g of hydroxypropyl-$\beta$-cyclodextrin (DS= 0.9) were used as the cyclodextrin.

An ethylene/vinyl acetate copolymer with an ethylene content of 12.0% by weight, a vinyl acetate content of 87.6% by weight and 0.4% by weight of AMPS resulted. The dispersion had no coarse fraction and had a solids content of 55% by weight, a pH of 3.0 and an average particle size of 260 nm.

EXAMPLE 11

The procedure was analogous to Example 9, with the difference that 355 g of hydroxypropyl-$\beta$-cyclodextrin (DS= 0.9) were used as the cyclodextrin.

An ethylene/vinyl acetate copolymer with an ethylene content of 12.0% by weight, a vinyl acetate content of 87.6% by weight and 0.4% by weight of AMPS resulted. The dispersion had no coarse fraction and had a solids content of 49.6% by weight, a pH of 3.0 and an average particle size of 500 nm.

EXAMPLE 12

The procedure was analogous to Example 9, with the difference that 131 g of methyl-$\beta$-cyclodextrin (DS=0.6) were used as the cyclodextrin.

An ethylene/vinyl acetate copolymer with an ethylene content of 9.0% by weight, a vinyl acetate content of 90.5% by weight and 0.5% by weight of AMPS resulted. The dispersion had no coarse fraction and had a solids content of 52.3% by weight, a pH of 4.9 and an average particle size of 770 nm.

EXAMPLE 13

The procedure was analogous to Example 9, with the difference that 218 g of methyl-$\beta$-cyclodextrin (DS=1.8) were used as the cyclodextrin.

An ethylene/vinyl acetate copolymer with an ethylene content of 15.0% by weight, a vinyl acetate content of 84.6% by weight and 0.4% by weight of AMPS resulted. The dispersion had no coarse fraction and had a solids content of 50.9% by weight, a pH of 2.9 and an average particle size of 500 nm.

EXAMPLE 14

2480 g of completely desalinated water, 143 g of a 20% strength aqueous solution of the sodium salt of dihexylsulfosuccinate and 52.3 ml of 10% strength acetic acid were initially introduced into a pressure reactor. The pH of the initial mixture was brought to 4.0 with 10% strength sodium hydroxide solution. 714 g of vinyl acetate were emulsified in, while stirring, and the mixture was heated up to 75° C. When temperature equilibrium had been reached, up to 25 bar of ethylene were forced in. Metering in of solutions of 53.7 g of potassium peroxodisulfate in 1730 g of water and 26.8 g of hydroxymethanesulfinic acid in 1760 g of water was then started simultaneously. After the start of the reaction, 6430 g of vinyl acetate and a solution of 714 g of 30% strength sodium lauryl polyglycol sulfate, 71.4 g of 50% strength sodium acrylamido-2-methylpropanesulfonate and 143 g of acetyl-$\beta$-cyclodextrin (DS =1.0) in 3570 g of water were metered in continuously. When the monomer and emulsifier feed had ended, also no further ethylene was fed in and the initiator system was still metered in further until the solids content of the dispersion no longer rose. The mixture was then cooled and the autoclave was let down. To bring the polymerization to completion, 61 ml of 10% strength aqueous tert-butyl hydroperoxide solution and 6 ml of 10% strength aqueous hydroxymethanesulfinic acid solution were now added.

An ethylene/vinyl acetate copolymer with an ethylene content of 9.0% by weight, a vinyl acetate content of 90.5% by weight and 0.5% by weight of AMPS resulted. The dispersion contained hardly any coarse fraction and had solids content of 51.7% by weight, a pH of 3.3 and an average particle size of 240 nm.

EXAMPLE 15

Example 15 was carried out analogously to Example 14 348 g of acetyl-$\beta$-cyclodextrin being employed instead of 143 g of acetyl-$\beta$-cyclodextrin.

An ethylene/vinyl acetate copolymer with an ethylene content of 15.0% by weight, a vinyl acetate content of 84.6% by weight and 0.4% by weight of AMPS resulted. The dispersion contained hardly any coarse fraction and had solids content of 50.4% by weight, a pH of 3.1 and a average particle size of 310 nm.

EXAMPLE 16

341 g of completely desalinated water, 18.5 g of a 20% strength aqueous solution of the sodium salt of dihexylsulfosuccinate and 5.41 g of 10% strength acetic acid were initially introduced into a glass reactor. The pH of the initial mixture was brought to 4.0 with 10% strength sodium hydroxide solution. 36.9 g each of styrene and butyl acrylate were emulsified in, while stirring, and the mixture was heated up to 50° C. 288 g of water, 45.2 g of 30% strength sodium lauryl polyglycol sulfate, 73.8 g of 30% strength acrylamide, 332 g of styrene, 332 g of butyl acrylate and 36.9 g of acetyl-β-cyclodextrin (DS=1.0) were pre-emulsified in a metering container. The pH of the pre-emulsion was brought to 4.0 with 10% strength acetic acid. Metering in of solutions of 11.6 g of 40% strength tert-butyl hydroperoxide in 144 g of water and 7.95 g of hydroxymethanesulfinic acid in 148 g of water was then started simultaneously, while stirring. After the start of the reaction, the pre-emulsion was metered in uniformly. When the pre-emulsion feed had ended, the initiator system was still metered in further until the solids content of the dispersion no longer rose. The mixture was then cooled. To bring the polymerization to completion, 4.8 ml of 10% strength aqueous tert-butyl hydroperoxide solution and 4.8 g of 10% strength aqueous hydroxymethanesulfinic acid solution were now added.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 48.2% by weight, a pH of 3.3 and an average particle size of 220 nm.

EXAMPLE 17

Example 17 was carried out analogously to Example 16, 15.2 g of acetyl-β-cyclodextrin being employed instead of 36.9 g of acetyl-β-cyclodextrin.

A styrene/butyl acrylate copolymer with a styrene content of 48.5% by weight, a butyl acrylate content of 48.5% by weight and 3.0% by weight of acrylamide resulted. The dispersion contained hardly any coarse fraction and had a solids content of 48.0% by weight, a pH of 3.4 and an average particle size of 250 nm.

EXAMPLE 18

2.38 kg of completely desalinated water, 129 g of a 20% strength aqueous solution of the sodium salt of dihexylsulfosuccinate, 37.9 g of 10% strength acetic acid and 259 g of hydroxypropyl-β-cyclodextrin (DS=0.9) were initially introduced into a glass reactor. The pH of the initial mixture was brought to 4.0 with 10% strength sodium hydroxide solution. 228 g of styrene and 290 g of butyl acrylate were emulsified in, while stirring, and the mixture was heated up to 50° C. 2.02 kg of water, 345 g of 30% strength sodium lauryl polyglycol sulfate, 517 g of 30% strength acrylamide, 2.05 kg of styrene and 2.61 kg of butyl acrylate were pre-emulsified in a metering container. The pH of the pre-emulsion was brought to 4.0 with 10% strength acetic acid. Metering in of solutions of 81.6 g of 40% strength tert-butyl hydroperoxide in 1.00 kg of water and 55.7 g of hydroxymethanesulfinic acid in 1.03 kg of water was then started simultaneously, while stirring. After the start of the reaction, the pre-emulsion was metered in uniformly. When the pre-emulsion feed had ended, the initiator system was still metered in further until the solids content of the dispersion no longer rose. The mixture was then cooled. To bring the polymerization to completion, 34 g of 10% strength aqueous tert-butyl hydroperoxide solution and 34 g of 10% strength aqueous hydroxymethanesulfinic acid solution were now added.

A styrene/butyl acrylate copolymer with a styrene content of 42.7% by weight, a butyl acrylate content of 54.4% by weight and 2.9% by weight of acrylamide resulted. The glass transition temperature was 10° C. The dispersion contained hardly any coarse fraction and had a solids content of 44.2% by weight, a pH of 3.3 and an average particle size of 280 nm.

EXAMPLE 19

The procedure was analogous to Example 18, with the difference that the initial mixture comprised 212 g of styrene and 305 g of butyl acrylate, and 1.91 kg of styrene were metered in together with 2.75 kg of butyl acrylate as a pre-emulsion.

A styrene/butyl acrylate copolymer with a styrene content of 39.8% by weight, a butyl acrylate content of 57.3% by weight and 2.9% by weight of acrylamide resulted. The glass transition temperature was 5° C. The dispersion contained hardly any coarse fraction and had a solids content of 45.2% by weight, a pH of 3.2 and an average particle size of 390 nm.

EXAMPLE 20

The procedure was analogous to Example 18, with the difference that the initial mixture comprised 219 g of styrene and 290 g of ethylhexyl acrylate, and 1.97 kg of styrene were metered in together with 2.61 kg of ethylhexyl acrylate as a pre-emulsion.

A styrene/ethylhexyl acrylate copolymer with a styrene content of 41.7% by weight, a ethylhexyl acrylate content of 55.3% by weight and 3.0% by weight of acrylamide resulted. The glass transition temperature was -5° C. The dispersion contained hardly any coarse fraction and had a solids content of 44.9% by weight, a pH of 3.6 and an average particle size of 430 nm.

EXAMPLE 21

17.0 kg of completely desalinated water, 923 g of a 20% strength aqueous solution of the sodium salt of dihexylsulfosuccinate, 270 g of 10% strength acetic acid and 1.85 kg of hydroxypropyl-β-cyclodextrin (DS=0.9) were initially introduced into a polymerization tank. The pH of the initial mixture was brought to 4.1 with 10% strength sodium hydroxide solution. 1.85 kg each of styrene and butyl acrylate were emulsified in, while stirring, and the mixture was heated up to 50° C. 14.4 kg of water, 2.46 kg of 30% strength sodium lauryl polyglycol sulfate, 16.6 kg of styrene and 16.6 kg of butyl acrylate were pre-emulsified in a metering container. The pH of the pre-emulsion was brought to 4.1 with 10% strength acetic acid. Metering of solutions of 581 g of 40% strength tert-butyl hydroperoxide in 7.17 kg of water and 399 g of hydroxymethanesulfinic acid in 7.39 kg of water was then started simultaneously, while stirring. After the start of these meterings, the pre-emulsion was metered in uniformly. When the pre-emulsion feed had ended, the initiator system was still metered in further until the solids content of the dispersion no longer rose. The mixture was then cooled. To bring the polymerization to completion, 240 ml of 10% strength aqueous tert-butyl hydroperoxide solution and 240 g of 10% strength aqueous hydroxymethanesulfinic acid solution were now added. A styrene/butyl acrylate copolymer with a styrene content of 50.0% by weight, a butyl acrylate content of 50.0% by weight resulted. The dispersion contained hardly any coarse fraction and had a solids content of 45.7% by weight, a pH of 3.4 and an average particle size of 300 nm.

EXAMPLE 22

264 g of completely desalinated water, 15.2 g of a 20% strength aqueous solution of the sodium salt of dihexylsulfosuccinate and 5.57 ml of of 10% strength acetic acid were initially introduced into a laboratory autoclave. The pH of the initial mixture was brought to 4.0 with 10% strength sodium hydroxide solution. 76 g of vinyl acetate were emulsified in, while stirring, and the mixture was heated up to 75° C. When temperature equilibrium had been reached, up to 25 bar of ethylene were forced in. 380 g of water, 15.2 g of acetyl-β-cyclodextrin (DS=1.0), 7.6 g of 50% strength sodium acrylamido-2-methylpropanesulfonate, 76.0 g of 30% strength sodium lauryl polyglycol sulfate and 684 g of vinyl acetate were emulsified in a pre-emulsion vessel. Metering in of solutions of 6.65 g of potassium peroxodisulfate in 215 g of water and 3.33 g of hydroxymethanesulfinic acid in 218 g of water was then started simultaneously, while stirring. After the start of the reaction, the pre-emulsion was metered in continuously. During this period, the ethylene pressure was kept at 25 bar. The ethylene feed was then closed and the initiator system was still metered in further until the solids content of the dispersion no longer rose. The mixture was then cooled and the autoclave was let down. To bring the polymerization to completion, 6.5 ml of 10% strength aqueous tert-butyl hydroperoxide solution and 6.5 ml of 10% strength aqueous hydroxymethanesulfinic acid solution were now added.

An ethylene/vinyl acetate copolymer with an ethylene content of 15.0% by weight, a vinyl acetate content of 84.6% by weight and 0.4% by weight of AMPS resulted. The dispersion contained hardly any coarse fraction and had a solids content of 53.2% by weight, a pH of 3.4 and an average particle size of 330 nm.

Preparation of the dispersion powders:

EXAMPLE 23

4000 parts by weight of the dispersion from Example 5 and 244.9 parts by weight of phenolsulfonic acid-formaldehyde condensate as a 51.0% strength solution in water (7.0% by weight, based on the dispersion solids content) were mixed thoroughly. The mixture was sprayed through a two-component nozzle. Air precompressed to 4 bar served as the spraying component; the drops formed were dried in co-current with air heated to 95° C. 10.0% by weight, based on the total weight of polymeric constituents, of a commercially available antiblocking agent (mixture of calcium magnesium carbonate and magnesium hydrosilicate) was added to the resulting powder.

EXAMPLE 24

4000 parts by weight of the dispersion from example 5 and 426.7 parts by weight of naphthalene-sulfonic acid-formaldehyde condensate as a 30.0% strength solution in water (7.0% by weight, based on the dispersion solids content) were mixed thoroughly. The mixture was sprayed through a two-component nozzle. Air precompressed to 4 bar served as the spraying component; the drops formed were dried in co-current with air heated to 80° C. 10.0% by weight, based on the total weight of polymeric constituents, of a commercially available antiblocking agent (mixture of calcium magnesium carbonate and magnesium hydrosilicate) was added to the resulting powder.

EXAMPLE 25

4000 parts by weight of the dispersion from Example 5 and 609.3 parts by weight of naphthalene-sulfonic acid-formaldehyde condensate as a 30.0% strength solution in water (10.0% by weight, based on the dispersion solids content) were mixed thoroughly. The mixture was sprayed through a two-component nozzle. Air precompressed to 4 bar served as the spraying component; the drops formed were dried in co-current with air heated to 80° C. 5.0% by weight, based on the total weight of polymeric constituents, of a commercially available antiblocking agent (mixture of calcium magnesium carbonate and magnesium hydrosilicate) was added to the resulting powder.

COMPARISON EXAMPLE 3

4000 parts by weight of the dispersion from Comparison Example 2 and 664.7 parts by weight of phenolsulfonic acid-formaldehyde condensate as a 43.6% strength solution in water (15.0% by weight, based on the dispersion solids content) were mixed thoroughly. The mixture was sprayed through a two-component nozzle. Air precompressed to 4 bar served as the spraying component; the drops formed were dried in co-current with air heated to 80° C. 5% by weight, based on the total weight of polymeric constituents, of a commercially available antiblocking agent (mixture of calcium magnesium carbonate and magnesium hydrosilicate) was added to the resulting powder.

Use Studies

In the tests to determine the flexural tensile, compressive and adhesive strengths, a DIN mortar according to DIN 1164 was employed. A plastic/cement value of P/C=0.15 (P/C=0.15 means 15% by weight of dispersion powder based on the amount of cement employed) was used in all the tests. Recipe of the DIN mortar according to DIN 1164:

| | |
|---|---|
| Portland cement PZ-35F | 900 g |
| Standard sand (= 2 bags) | 2700 g |
| Silicone defoamer S-860 (Wacker Chemie) | 7.2 g |
| Dispersion powder | 135 g |
| Water | 360 g |

The pulverulent constituents of the recipe were mixed together with the dispersion powder from the Examples or the Comparison Example to give a dry mortar.

The dry mortar was then brought to the corresponding water/cement value (W/C) of 0.40 (mortar without added powder and Comparison Example 3 only possible with W/C=0.45) with water and mixed.

Testing of the crude mortar properties shows the highly water-saving and liquefying properties of the dispersion powders according to the invention (Examples 23, 24, 25). The results are summarized in Table 1.

TABLE 1

Crude mortar data

| Dispersion powder | P/C | Air content (%) | Slump without vibrating (cm) | Slump after vibrating (cm) |
|---|---|---|---|---|
| without dispersion powder | 0.45 | 3.7 | 10.0 | 13.0 |
| Example 23 | 0.40 | 1.5 | 14.5 | 20.5 |
| Example 24 | 0.40 | 4.3 | 10.0 | 16.0 |
| Example 25 | 0.40 | 4.0 | 11.5 | 18.0 |
| Comparison Example 3 | 0.45 | 4.2 | 10.0 | 16.5 |

For testing of the flexural tensile strength and compressive strength, mortar prisms of dimensions 160×40×40 mm according to DIN 1164 were produced. The test specimen were removed from the form in each case two days after filling of the form. During this period, the form was covered.

The results of the flexural tensile and compressive strength tests are summarized in Table 2. The results show a significant increase in the flexural tensile strength by the addition of the dispersion powders according to the invention compared with the mortar without added dispersion powder or with Comparison Example 3. In contrast to the powder from Comparison Example 3, the compressive strength of the mortar prisms is influenced only slightly by the addition of the dispersion powders according to the invention.

TABLE 2

Flexural tensile/compressive strength after storage in a standard climate (23° C., 50% relative humidity) for 28 days

| Dispersion powder | Flexural tensile strength (N/mm²) | Compressive strength (N/mm²) |
| --- | --- | --- |
| without dispersion powder | 7.88 ± 0.35 | 47.2 ± 2.2 |
| Example 23 | 13.41 ± 0.44 | 49.8 ± 1.1 |
| Example 24 | 12.13 ± 1.10 | 46.1 ± 0.7 |
| Example 25 | 12.81 ± 0.53 | 47.3 ± 1.2 |
| Comparison Example 3 | 8.92 ± 0.24 | 39.8 ± 1.0 |

To test the adhesive strength, the mortars were absorbed onto concrete quarry tiles (B550, 40×40 cm²) stored in a standard climate (23° C., 50% relative atmospheric humidity) in a layer thickness of 4 mm by means of a spray applicator using a template. The tiles were stored in the standard climate. One day before the test date, 6 test specimens per tile were drilled out with a core drill and circular pull-off clamps (diameter 55 mm, thickness 10 mm) were glued on with a two-component adhesive. The clamps were pulled off with a pull-off apparatus at a rate of increase in load of 250N/second.

The results of the adhesive strength tests are summarized in Table 3. The results of this test show a significant increase in the adhesive strength when the dispersion powders according to the invention (Examples 23, 24, 25) are employed compared with the use of the powder from Comparison Example 3 and the mortar without added dispersion powder.

TABLE 3

Adhesive strength after storage in a standard climate (23° C., 50% relative humidity) for 28 days

| Dispersion powder | Adhesive strength (N/mm²) |
| --- | --- |
| without dispersion powder | 1.38 ± 0.11 |
| Example 23 | 3.06 ± 0.17 |
| Example 24 | 2.83 ± 0.15 |
| Example 25 | 3.19 ± 0.16 |
| Comparison Example 3 | 1.81 ± 0.14 |

TABLE 4

Composition of the polymer dispersions

| Example | Copolymer | Comonomers (% by weight) | Cyclo-dextrin | Amount of CD (% by weight) | DS | Tg (°C.) | FC (%) | pH | Particle size (nm) |
| --- | --- | --- | --- | --- | --- | --- | --- | --- | --- |
| C.Ex. 1 | VAc/E/AMPS | 84.6/15.0/0.4 | — | — | — | 10 | 49.8 | 4.0 | 310 |
| C.Ex. 2 | St/BA/AA | 48.5/48.5/3.0 | — | — | — | 20 | 49.0 | 3.5 | 210 |
| Ex. 1 | St/BA/AA | 48.5/48.5/3.0 | α-CD | 5.0 | — | 20 | 44.6 | 3.7 | 350 |
| Ex. 2 | St/BA/AA | 48.5/48.5/3.0 | β-CD | 5.0 | — | 15 | 48.2 | 4.4 | 300 |
| Ex. 3 | St/BA/AA | 48.5/48.5/3.0 | γ-CD | 5.0 | — | 15 | 46.7 | 3.7 | 260 |
| Ex. 4 | St/BA/AA | 48.5/48.5/3.0 | Ac-β-CD | 5.0 | 1.0 | 15 | 46.2 | 3.3 | 290 |
| Ex. 5 | St/BA/AA | 48.5/48.5/3.0 | Hp-β-CD | 5.0 | 0.9 | 15 | 45.7 | 3.4 | 300 |
| Ex. 6 | St/BA/AA | 48.5/48.5/3.0 | Hp-β-CD | 2.0 | 0.9 | 15 | 46.9 | 4.0 | 1700 |
| Ex. 7 | St/BA/AA | 48.5/48.5/3.0 | Me-β-CD | 5.0 | 0.6 | 15 | 44.8 | 4.1 | 2000 |
| Ex. 8 | St/BA/AA | 48.5/48.5/3.0 | CMe-β-CD | 5.0 | 0.3 | 15 | 43.2 | 4.2 | 300 |
| Ex. 9 | VAc/E/AMPS | 84.6/15.0/0.4 | Ac-β-CD | 5.0 | 1.0 | 5 | 50.5 | 3.2 | 570 |
| Ex. 10 | VAc/E/AMPS | 87.6/12.0/0.4 | Hp-β-CD | 2.0 | 0.9 | 10 | 55.0 | 3.0 | 260 |
| Ex. 11 | VAc/E/AMPS | 87.6/12.0/0.4 | Hp-β-CD | 5.0 | 0.9 | 10 | 49.6 | 3.0 | 500 |
| Ex. 12 | VAc/E/AMPS | 90.5/9.0/0.5 | Me-β-CD | 5.0 | 0.6 | 15 | 52.3 | 4.9 | 770 |
| Ex. 13 | VAc/E/AMPS | 84.6/15.0/0.4 | Me-β-CD | 5.0 | 1.8 | 5 | 50.9 | 2.9 | 500 |
| Ex. 14 | VAc/E/AMPS | 90.5/9.0/0.5 | Ac-β-CD | 2.0 | 1.0 | 15 | 51.7 | 3.3 | 240 |
| Ex. 15 | VAc/E/AMPS | 84.6/15.0/0.4 | Ac-β-CD | 5.0 | 1.0 | 5 | 50.4 | 3.1 | 310 |
| Ex. 16 | St/BA/AA | 48.5/48.5/3.0 | Ac-β-CD | 5.0 | 1.0 | 15 | 48.2 | 3.3 | 220 |
| Ex. 17 | St/BA/AA | 48.5/48.5/3.0 | Ac-β-CD | 2.0 | 1.0 | 15 | 48.0 | 3.4 | 250 |
| Ex. 18 | St/BA/AA | 42.7/54.4/2.9 | Hp-β-CD | 5.0 | 0.9 | 10 | 44.2 | 3.3 | 280 |
| Ex. 19 | St/BA/AA | 39.8/57.3/2.9 | Hp-β-CD | 5.0 | 0.9 | 5 | 45.2 | 3.2 | 390 |
| Ex. 20 | St/EHA/AA | 41.7/55.3/3.0 | Hp-β-CD | 5.0 | 0.9 | −5 | 44.9 | 3.6 | 430 |
| Ex. 21 | St/BA | 50.0/50.0 | Hp-β-CD | 5.0 | 0.9 | 15 | 45.7 | 3.4 | 300 |
| Ex. 22 | VAc/E/AMPS | 84.6/15.0/0.4 | Ac-β-CD | 2.0 | 1.0 | 5 | 53.2 | 3.4 | 330 |

We claim:

1. A redispersible polymer powder composition which comprises a homo- or copolymer of ethylenically unsaturated monomers and a cyclodextrin or cyclodextrin derivative of the general formula

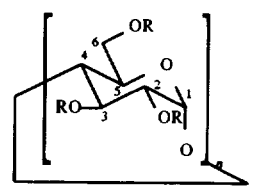

(I)

in which n =6, 7 or 8 and R is identical or different and has the meaning of H or $R^1$, where $R^1$ is identical or different and has the meaning of optionally substituted $C_1-C_4$-alkyl, hydroxy-$C_1-C_4$-alkyl, carboxy-$C_1-C_4$-alkyl or $C_2-C_4$-carboxyl radicals.

2. A redispersible polymer powder composition as claimed in claim 1, which comprises a homo- or copolymer comprising one or more monomer units selected from the group consisting of vinyl esters of unbranched or branched carboxylic acids having 1 to 18 C atoms, esters of acrylic acid and methacrylic acid with unbranched or branched alcohols having 1 to 18 C atoms, vinylaromatics, halides and olefins.

3. A redispersible polymer powder composition as claimed in claim 1, which comprises as the cyclodextrin α-cyclodextrin (cyclohexaamylose, formula I: n=6, R=H), β-cyclodextrin (cycloheptaamylose, formula I: n=7, R=H), γ-cyclodextrin (cyclooctaamylose, formula I: n=8, R=H) or a mixture of the cyclodextrins mentioned.

4. A redispersible polymer powder composition as claimed in claim 1, which comprises as the cyclodextrin derivative one or more derivatives from the group consisting of the methyl ethers, ethyl ethers or propyl ethers of α-, β- and γ-cyclodextrin; the hydroxyethyl, hydroxypropyl and dihydroxypropyl ethers of α-, β- and γ-cyclodextrin; the carboxymethyl and carboxypropyl ethers of α-, β- and γ-cyclodextrin; the mixed ethers of α-, β- and γ-cyclodextrin which contain at least two different groups of the alkyl ether, hydroxyalkyl ether or carboxyalkyl ether groups mentioned; the acetic acid esters (acetyl-cyclodextrins) and propionic acid esters (propionyl-cyclodextrins) of α-, β- and γ-cyclodextrin; or 2-aminoethyl- or 2-chloroacetyl-cyclodextrin.

5. A redispersible polymer powder composition as claimed in claim 1, wherein the average degree of substitution (DS value) of the cyclodextrin derivatives is 0.5 to 2.5.

6. A redispersible polymer powder composition as claimed in claim 1, wherein the polymer powder composition comprises 0.3 to 20% by weight of cyclodextrin or cyclodextrin derivatives, based on the polymer content.

7. A process for the preparation of a redispersible polymer powder composition which comprises a homo- or copolymer of ethylenically unsaturated monomers and cyclodextrin or a cyclodextrin derivative of the general formula (I) as claimed in claim 1 a) emulsion polymerization of one or more ethylenically unsaturated monomers by means of free radical initiators in an aqueous medium in the presence of cyclodextrin or a cyclodextrin derivative of the general formula (I) and if appropriate emulsifier and in the absence of protective colloids and b) drying of the aqueous polymer dispersion obtained by this procedure, if appropriate with the addition of antiblocking agents and/or further additives.

8. An aqueous polymer dispersion having a solids content of 30 to 75% by weight which comprises a homo- or copolymer of ethylenically unsaturated monomers and cyclodextrin or a cyclodextrin derivative of the general formula (I) as claimed in claim 1, obtainable by emulsion polymerization of one or more ethylenically unsaturated monomers by means of free radical initiators in an aqueous medium in the presence of cyclodextrin or a cyclodextrin derivative of the general formula (I) and if appropriate emulsifier and in the absence of a protective colloids.

9. Hydraulic binders containing as an additive, the redispersible polymer powder composition as claimed in claim 1

10. Coating compositions containing as a binder, the redispersible polymer powder composition as claimed in claim 1.

11. Adhesive compositions containing the redispersible polymer powder composition as claimed in claim 1.

12. Paper containing as a binder, the redispersible polymer powder composition as claimed in claim 1.

13. Compression molded articles containing as a binder the redispersible polymer powder composition as claimed in claim 1.

* * * * *